US008951783B2

(12) United States Patent
Bhattacharya

(10) Patent No.: US 8,951,783 B2
(45) Date of Patent: Feb. 10, 2015

(54) DETECTOR FOR CHEMICAL COMPOUNDS

(76) Inventor: Jaydeep Bhattacharya, Kolkata (IN)

(*) Notice: Subject to any disclaimer, the term of this patent is extended or adjusted under 35 U.S.C. 154(b) by 83 days.

(21) Appl. No.: 13/254,153

(22) PCT Filed: Nov. 23, 2010

(86) PCT No.: PCT/IB2010/002990
§ 371 (c)(1),
(2), (4) Date: Aug. 31, 2011

(87) PCT Pub. No.: WO2011/124945
PCT Pub. Date: Oct. 13, 2011

(65) Prior Publication Data
US 2012/0058508 A1 Mar. 8, 2012

(30) Foreign Application Priority Data

Apr. 7, 2010 (IN) .............................. 394/KOL/2010

(51) Int. Cl.
C12M 1/34 (2006.01)
C12M 3/00 (2006.01)
G01N 21/94 (2006.01)
G01N 21/51 (2006.01)
G01N 33/18 (2006.01)
G01N 1/38 (2006.01)
G01N 21/82 (2006.01)

(52) U.S. Cl.
CPC ................ G01N 21/94 (2013.01); G01N 21/51 (2013.01); G01N 33/1893 (2013.01); G01N 1/38 (2013.01); G01N 21/82 (2013.01)
USPC ..................... 435/288.7; 435/287.1

(58) Field of Classification Search
CPC . G01N 15/0826; G01N 15/08; G01N 15/082; G01N 15/0806; G01N 15/088; G01N 21/03; G01N 21/82; G01N 21/94; G01N 21/51; G01N 33/1893; G01N 1/38; B01L 2400/0406; B01L 2400/0481; B01L 3/502; B01L 2400/0666; B01L 2400/0655; B01L 2400/0644; B01L 2400/0638; B01L 2400/0633
USPC ........................................... 435/288.7, 287.1
See application file for complete search history.

(56) References Cited

U.S. PATENT DOCUMENTS 5,817,954 A * 10/1998 Kahng et al. .................... 422/75
6,589,779 B1 * 7/2003 McDevitt et al. ........... 435/288.7

(Continued)

FOREIGN PATENT DOCUMENTS

CN          1566958 A      1/2005
CN        201242545 Y      5/2009

(Continued)

OTHER PUBLICATIONS

Andersson, P.L. et al., "Ultraviolet absorption spectra of all 209 polychlorinated biphenyls evaluated by principal component analysis," Fresenius J Anal Chem, vol. 357, 1997, pp. 1088-1092.

(Continued)

Primary Examiner — Michael Marcheschi
Assistant Examiner — Timothy Barlow
(74) Attorney, Agent, or Firm — Foley & Lardner LLP

(57) ABSTRACT

Systems and methods to analyze contaminants including a plurality of stages configured to detect contaminants in a sample, wherein the plurality of stages are configured to detect a plurality of contaminants at substantially the same time.

12 Claims, 6 Drawing Sheets

(56) References Cited

U.S. PATENT DOCUMENTS

| | | | |
|---|---|---|---|
| 6,602,702 B1 * | 8/2003 | McDevitt et al. | 435/288.7 |
| 2003/0121313 A1 * | 7/2003 | Sparks | 73/38 |
| 2006/0240540 A1 * | 10/2006 | Nakatsuka | 435/287.2 |

FOREIGN PATENT DOCUMENTS

| | | |
|---|---|---|
| EP | 0 634 654 | 1/1995 |
| WO | WO-01/06239 | 1/2001 |
| WO | WO-2004/059324 | 7/2004 |
| WO | WO-2009/024774 | 2/2009 |

OTHER PUBLICATIONS

Chen, Y. et al., "Luminescent CdS Quantum Dots as Selective Ion Probes," Anal. Chem., Oct. 1, 2002, vol. 74, No. 19, pp. 5132-5138.

Garhart, M.D. et al., "Microdetermination of Aldrin and Dieldrin by Infrared Spectroscopy," Anal. Chem., May 1952, vol. 24, No. 5, pp. 851-857.

GE Analytical Instruments Profile on Environmental Expert, printed on Jul. 13, 2011, retrieved from the internet (http://www.environmental-expert.com/companies/ge-analytical-instruments-22510), 3 pages.

Graham, R.E. et al., "Detection and measurement of decomposition in endrin standards," J. Agric. Food Chem., Mar.-Apr. 1969, vol. 17, No. 2, pp. 259-263.

Hassoon, S. et al., "A sensitive fluorescence probe for DDT-type pesticides," Analytica Chimica Acta, 1998, vol. 368, pp. 77-82.

Arcoptix, "ARCoptix Fourier NIR and IR(Infrared) Spectrometer and Polarization Optics Products," printed on Jul. 21, 2011, retrieved from the internet (http://www.arcoptix.com/), 1 page.

International Search Report and Written Opinion for PCT/IB2010/002990 mailed Apr. 12, 2011.

Jin, W.J. et al., "Surface-modified CdSe quantum dots as luminescent probes for cyanide determination," Analytica Chimica Acta, 2004, vol. 522, pp. 1-8.

Kolhed, M. et al., "Assessment of quantum cascade lasers as mid infrared light sources for measurement of aqueous samples," Vibrational Spectroscopy, 2002, vol. 29, pp. 283-289.

Martinez, A. et al., "Use of UV Absorbance to Monitor Furans in Dilute Acid Hydrolysates of Biomass," Biotechnol, Prog., 2000, vol. 16, No. 4, pp. 637-641.

Maxion Technologies, Inc., "Single Mode Lasers," printed on Jun. 27, 2011, retrieved from the internet (http://www.maxion.com/singlemode.html), 2 pages.

Pereiro, R. et al., "Surface-modified water-soluble CdSe Quantum Dots as Luminescent Ion Probes," Poster, TNT2005, Aug. 29-Sep. 2, 2005, Oviedo-Spain, 2 pages.

Products and Equipment from GE Analytical Instruments on Environmental Expert, printed on Jul. 13, 2011, retrieved from the internet (http://www.environmental-expert.com/companies/ge-analytical-instruments-22510/products), 4 pages.

Reusch, "Infrared Spectroscopy," printed on Jun. 27, 2011, retrieved from the internet (http://www2.chemistry.msu.edu/faculty/reusch/VirtTxtJml/Spectrpy/Red/infrared.htm), 5 pages.

Future Electronics, printed on Jul. 21, 2011, retrieved from the internet (http://www.futureelectronics.com/en/Pages/index.aspx), 1 page.

* cited by examiner

| 300 Draw a sample |
|---|
| 302 Perform turbidity measurement |
| 304 Filter |
| 306 Add lysing agent |
| 307 Stir |
| 308 Perform biological measurement |
| 310 Filter |
| 312 Add stain if desired |
| 313 Stir |
| 314 Perform organic molecule measurement |
| 316 Filter |
| 318 Add quantum dots |
| 319 Stir |
| 320 Perform ion measurement |

Fig. 7

DETECTOR FOR CHEMICAL COMPOUNDS

CROSS-REFERENCE TO RELATED APPLICATIONS

The present application is a U.S. national stage application claiming the benefit of International Application No. PCT/IB2010/002990, filed on Nov. 23, 2010, which claims the benefit of Indian Application No. 394/KOL/2010, filed on Apr. 7, 2010, the entire contents of which are incorporated herein by reference in their entireties.

BACKGROUND

Natural water may be contaminated with industrial wastes that contain toxic end products. Further, pesticides used for protecting crops may also be washed into and contaminate the water supply. These toxic chemicals have been found to create health hazards and also to damage/destroy various ecosystems.

A class of bacteria that may be found in water supply includes coliforms. Indeed, coliforms are a commonly-used bacterial indicator of the sanitary quality of foods and water. The presence of coliforms may be used to indicate that other pathogenic organisms of fecal origin may be present. This is because feces from warm blooded animals or human beings often leads to the contamination of water by coliforms and other pathogenic organisms.

Coliforms include *E. coli, Salmonella, Klebsiella* and *Erwinia*. These pathogenic organisms may cause intestinal infections, dysentery, hepatitis, typhoid fever cholera etc. Further, coliforms and other chemical contaminants may have toxic effects on the habitants of a contaminated pond/lake, limiting their growth and proliferation.

BRIEF DESCRIPTION OF THE DRAWINGS

Features of the invention are shown in the drawings, in which like reference numerals designate like elements.

FIG. 7 is a flow chart of a method according to an embodiment.

DETAILED DESCRIPTION

Figure 1:
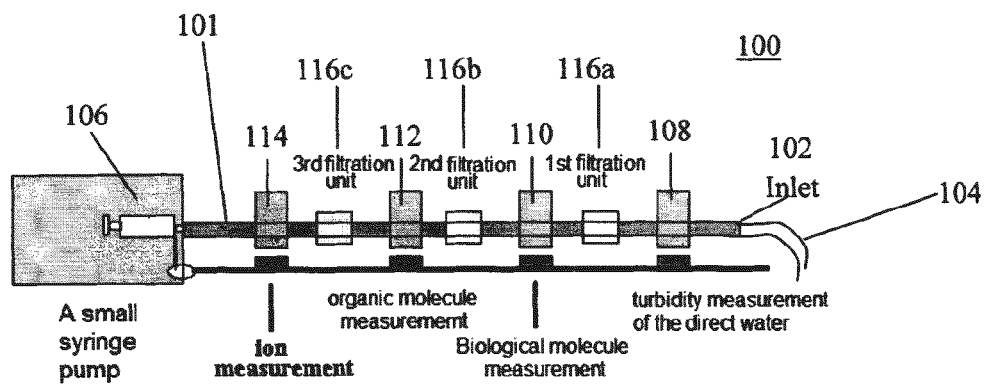
FIG. 1 is a schematic diagram of apparatus according to an embodiment.

The monitoring of the level of toxins in pond water is generally laborious and costly. An embodiment includes a low cost automatic optical or electronic apparatus to monitor water contamination that can be controlled remotely. In an embodiment, the apparatus can be remotely switched on and data collected. In some embodiments, a broad range contaminant profile of a body of water such as a pond or lake can be obtained. The profile may include turbidity measurements, bacterial count measurements, and measurements of dissolved organic and inorganic chemicals.

Embodiments include optical apparatuses and methods for analyzing pond/lake water. In an embodiment, the apparatus can enable measurement of a broad spectrum of commonly known contaminants of pond/lake water. Contaminants that may be measured include solutes, toxic organic compounds, heavy metal ions and toxic ions like cyanide. Embodiments of the instrument include the use of a simple fluidic systems, and the use of air pressure controlled valve systems for the addition of the reagents. In an embodiment, the apparatus can enable detection of several contaminants at the same times and reduce the use of manpower. In an embodiment the apparatus can includes light emitting diodes, diode detectors, simple fluidic systems and valve systems.

An embodiment relates to an apparatus comprising a plurality of stages configured to detect contaminants in a sample, where the plurality of stages are configured to detect a plurality of contaminants at substantial the same time. In an aspect, one of the plurality of stages is configured to measure turbidity of the sample. In another aspect, at least one of the plurality of stages is configured to measure the presence of biological organisms in the sample. In another aspect, at least one of the plurality of stages is configured to measure the presence of heavy metal ions in the sample. In another aspect, at least one of the plurality of stages is configured to measure the presence of organic compounds in the sample.

In another aspect, the compound is selected from the group consisting of poly-chlorinated biphenyls, dioxins, furans, aldrin, dieldrin, DDT, endrin, chlordane, haxachlorobenzene, mirex, toxaphene, and heptachlor. In another aspect, the apparatus comprises a plurality of stages configured to detect a plurality of different organic compounds. In another aspect, the sample is an aqueous solution. In another aspect, the apparatus further comprises at least one filtration unit. In another aspect, a stage comprises a sample holder, a light source, and a light detector. In another aspect, the light source comprises a light emitting diode (LED). In another aspect, the light detector comprises a diode. In another aspect, the apparatus is configured to be operated remotely.

An embodiment relates to a method comprising obtaining a sample, and analyzing the sample for the presence of biological organisms, heavy metal ions or organic compounds, wherein the analyzing is conducted in an apparatus having a plurality of different sensors configured to detect the presence of biological organisms, heavy metal ions and/or organic compounds at substantially the same time. In one aspect, the method further comprises measuring the turbidity of the sample. In another aspect, the method further comprises adding a lysing reagent to the sample. In another aspect, the method further comprises adding quantum dots to the sample. In another aspect, the method further comprises adding a stain to the sample. In another aspect, the method further comprises mixing the sample. In another aspect, the method further comprises filtering the sample. In another aspect, the apparatus is configured to be operated remotely.

FIG. 1 illustrates a schematic diagram of apparatus 100 according to an embodiment. The apparatus 100 of this embodiment includes a pipe/tube 101 which connects a series of stages. As illustrated, this embodiment includes four measurement stages: a turbidity stage 108, a biological measurement stage 110, an organic molecule stage 112, and an ion measurement stage 114. Other embodiments may include more or less stages. At one end of the pipe/tube 101 is an inlet 102 to which an optional hose 104 may be attached. The optional hose 104 may be extended into a pond or lake (or any other source of water to be tested). At the other end of the pipe/tube 101 is a pump 106. The pump 106 may be a syringe pump or any other kind of pump suitable to draw water from a water source into the inlet 102.

In some embodiment, the stages may be separated by filtration units 116a, 116b, and 116c. In the embodiment illustrated in FIG. 1, the turbidity stage 108, biological measurement stage 110, organic molecule stage 112, and ion measurement stage 114 are separated by filtration units 116a, 116b, and 116c, respectively. Other embodiments, however, may include more or less filtration units. That is, there may be more than one filtration unit between stages or stages having no filtration units between them. In one aspect, the filtration units 116a, 116b, and 116c, comprise multiuse filers. Multiuse filters can be used more than one time so that they do not have to be changed before each set of experiments. In another aspect, the filtration units 116a, 116b, and 116c, comprise single use, disposable filters. The choice of filter material is not important. That is, any filter medium having the specified pore size can be used. Further, the filtrations units 116a, 116b, and 116c are generally provided in such a manner that the sizes of the contaminant passed through the filtration units 116a, 116b, and 116c are in decreasing order. That is, the filtration units 116a, 116b, and 116c are configured in such a fashion so as to restrict passage of particles with larger diameter while allowing passage of particles with smaller diameter. For example, filtration unit 116a may include a filter with a pore size of approximately 2 micron or greater. The filter may be, for example, a glass microfiber grade D filter having a 2.7 micron porosity. If the size of the suspended particles is less than 2 microns, a 1.5 micron glass microfiber filter grade 934-AH may be used. Filtration unit 116b may include a filter having a pore size less than 1 micron. The filter may be, for example, a syringe filter including mixed cellulose (Millipore WMCF134501, pore size 0.45 micron). Filtration unit 116c may include a filter having a pore size between 0.1 and 0.3 micron. The filter may be, for example, a syringe filter including PTFE (Teflon®), (Millipore WPTF134501, pore size 0.22 micron). Suitable filters may be obtained, for example, from Millipore Corporation.

Figure 2:
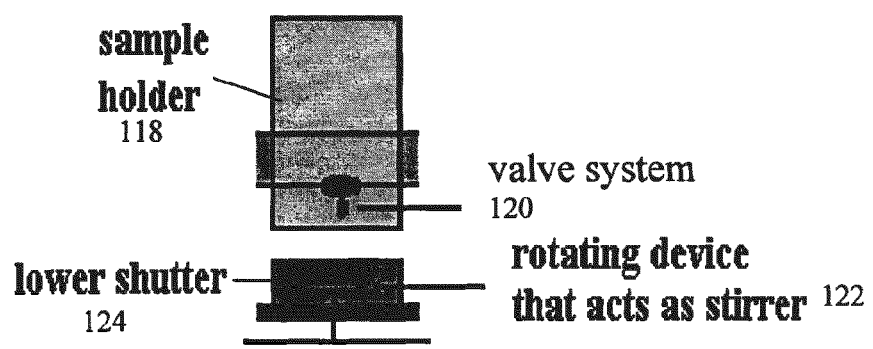
FIG. 2 is a schematic diagram of a sample holder according to an embodiment.
Figure 3:
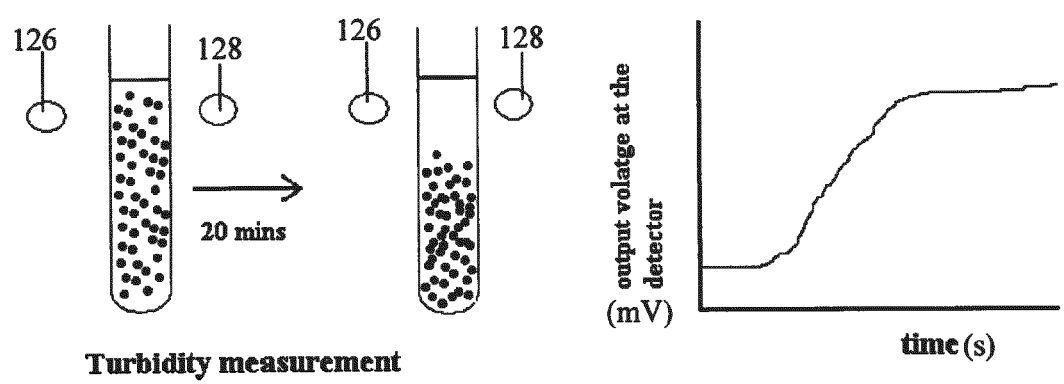
FIG. 3 is a schematic diagram of a turbidity measurement according to an embodiment.

FIG. 2 illustrates a sample holder 118 (e.g. a cuvette) according to an embodiment. The sample holder 118 may be of known dimensions and known volume. In an example embodiment an optical measurement technique is used. In this case, the sample holder 118 may be at least partially transparent to the light used for measurement. FIG. 3 illustrates an example of an optical measurement technique to measure turbidity. A water sample is taken and light from a light source 126 (e.g., and LED) is shown through the sample. The transmitted light is detected with a light detector 128 and converted to a voltage signal. The voltage signal is monitored as a function of time. As the particulate matter in the water settles, more light passes through the sample resulting in an increase in the voltage. The turbidity can then be determined as discussed in more detail below. With a transparent (partially transparent) sample holder 118, the light sources 126 and the light detectors 128 may be located outside of the sample holder 118. As the detectors 128 and light sources 126 are outside of the sample holder 118, and thus not in contact with the experimental samples, they typically will not get soiled. The light sources 126 may be of any type such as incandescent bulbs, light emitting diodes (LEDs), lasers or any other suitable light source. The light detectors may include, but are not limited to, diode detectors. Suitable light sources can be obtained from companies such as Maxion Technologies, Inc. Suitable light detectors can be obtained from companies such as Arcoptix S.A. and Future Electronics, Inc.

Optionally, a stirrer 122 can be included in the sample holder 118 and used to homogenize the sample. The stirrer 122 may also be used to stir reagents added to the sample as discussed in more detail below. The sample holder 118 may also include a lower shutter 124. The lower shutter 123 may be opened after the measurements are completed to empty the sample holder 118 and/or to allow access to the interior of the sample holder 118 to facilitate cleaning. The lower shutter 124 may also include a stirrer 122 comprising a rotatable bar connected to a rotor. The stirrer 122 may be used for making homogeneous solutions. Alternatively, a magnetic stirrer could be used.

Figure 4:
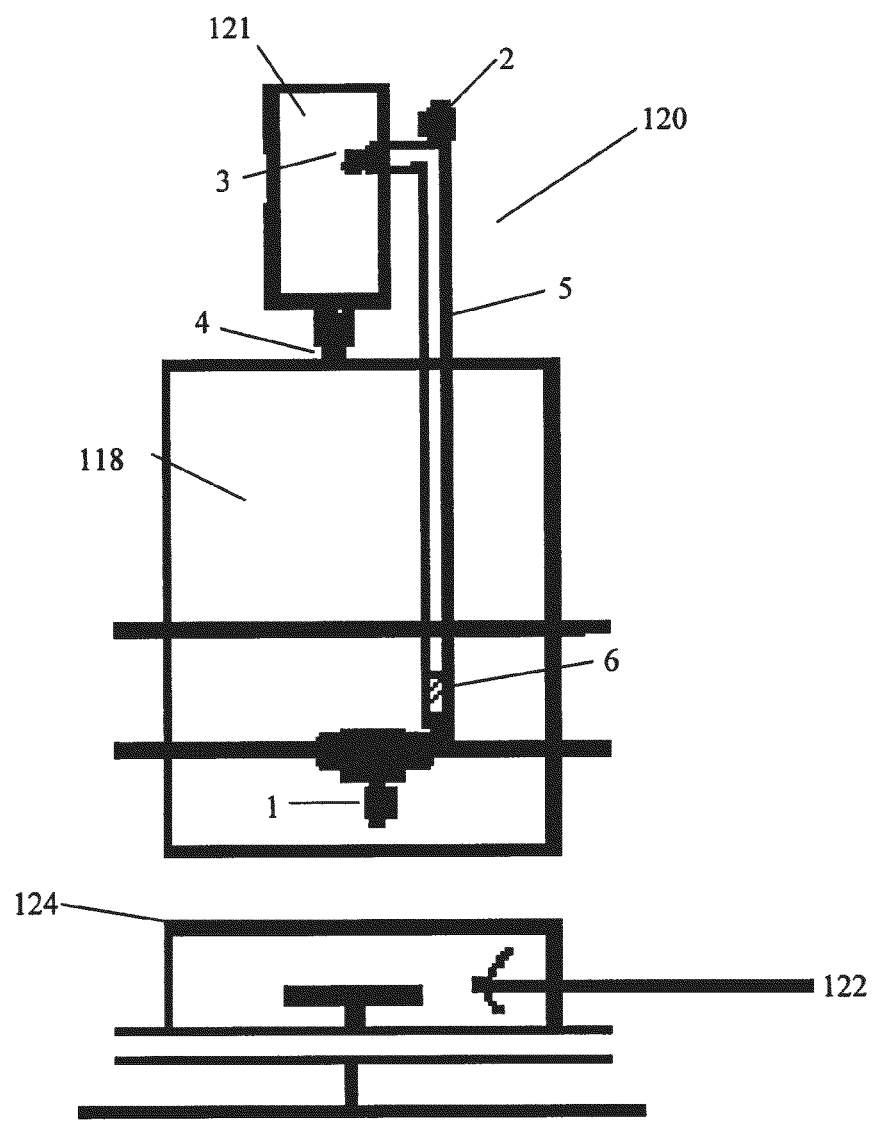
FIG. 4 is a schematic diagram of a valve system according to an embodiment.

Referring to FIG. 4, the sample holder 118 includes a float valve 1 which opens when the sample holder 118 is empty. When the sample holder 118 fills to a desired level, the float valve 1 valve closes. In this manner, each sample holder 118 may be filled with a water sample to be tested (FIG. 2). In one embodiment, separate sample holders 118 are provided for each contaminant to be measured. In this manner, all of the contaminants can be measured individually at the same time. In an alternative embodiment, multiple contaminants can be determined in a give sample holder 118. That is, the number of sample holders 118 may be less than the numbers of contaminants to be measured. In this embodiment, the measurement of the contaminants is generally performed sequentially rather than at the same time.

Figure 5:
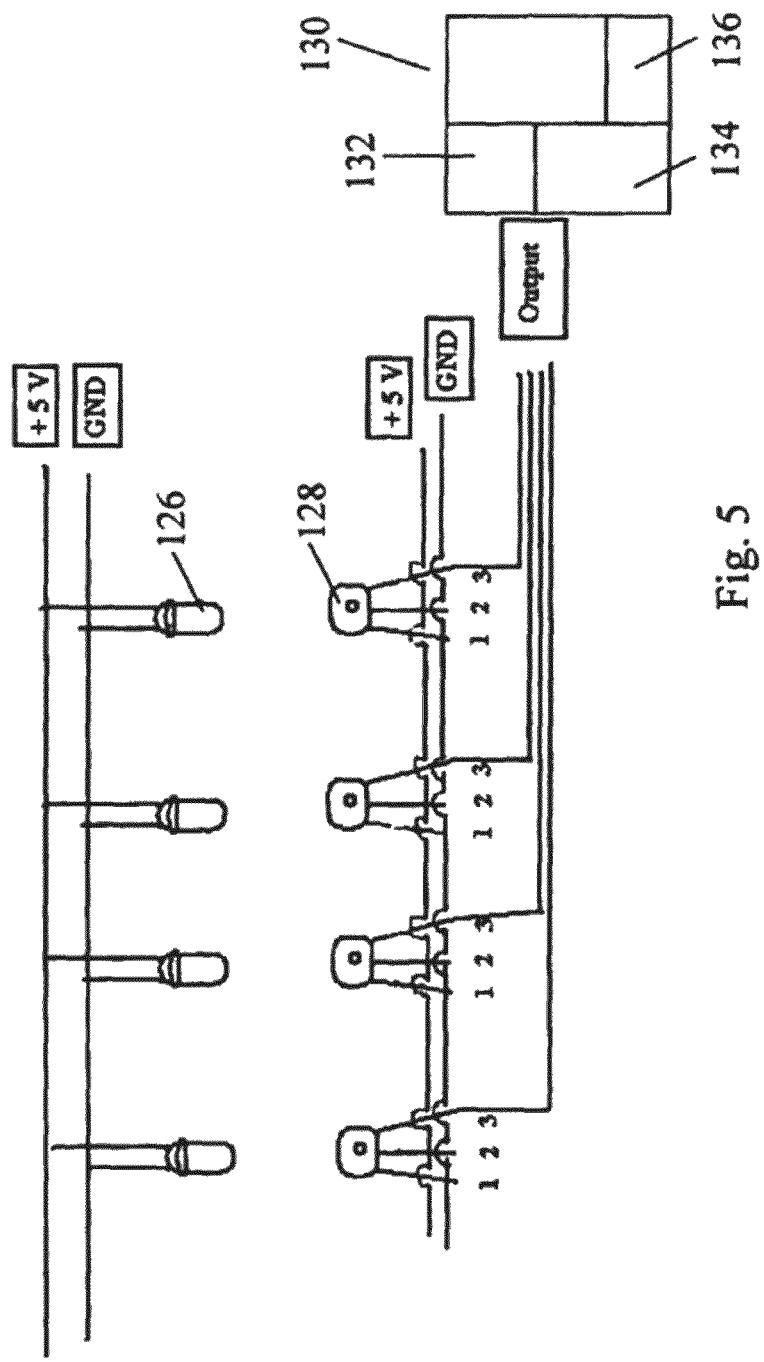
FIG. 5 is a schematic diagram of an LED circuit according to an embodiment.

In an embodiment, to detect if a particular toxin is present in the sample and/or measure the concentration of the toxin, light sources 126 (e.g., light emitting diodes) and light detectors 128 (e.g., diode detectors) can be configured in some or all of the stages (FIGS. 3, 5). That is, one or more stages may be configured with one or more light sources 126 on one side of the sample holder 118 and one or more light detectors 128 located on the opposite side of the sample holder 118. The concentration of the contaminant may be determined by measuring the absorption of light at a known wavelength and comparing the absorption to known absorption standards for the contaminant.

FIG. 4 illustrates an embodiment of a reagent delivery system 120 that may be used in conjunction with apparatus 100. As illustrated, the reagent delivery 120 includes four valves: a float valve 1, air intake valve 2, reagent reservoir valve 3, and reagent supply valve 4. The illustrated reagent delivery system 120 also includes a reagent reservoir 121, a reagent delivery piston 6, and a pressure tube 5 operatively connecting the reagent delivery piston 6 to the reagent reservoir 121. In this embodiment, the reagent delivery piston 6 is attached to the float valve 1 (which controls the water flow inside the sample holder 118). As the float valve 1 rises upon filling the sample holder 118 with a water sample, the delivery piston 6 asserts pressure in the pressure tube 5. The pressure causes reagent reservoir valve 3 and reagent delivery valve 4 to open and deliver an aliquot of the reagent to the sample holder 118. Afterwards, when the experiments are completed and the sample are drained out of the sample holder 118, the reagent delivery piston 6 may be dragged down and air valve 2 opened. When air valve 2 is opened, air is pulled into the pressure tube 5, preparing the reagent delivery system 120 for the next experiment.

Figure 6:
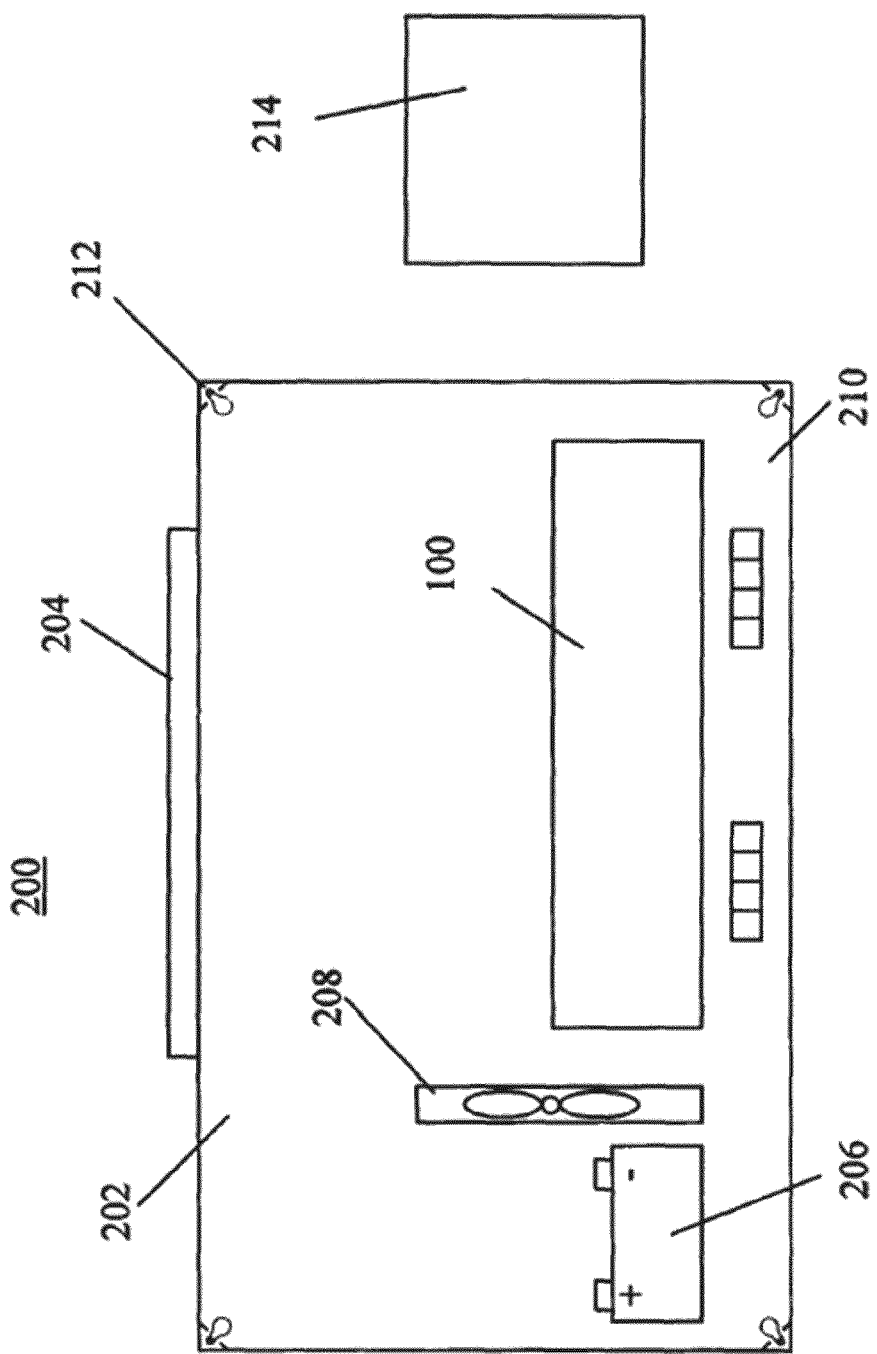
FIG. 6 is a schematic illustration of system according to an embodiment.

FIG. 5 is a circuit diagram illustrating the configuration of four light sources 126 and four light detectors 128 according to an embodiment of the apparatus 100. This embodiment includes four LEDs 126 and four diode detectors 128. In this embodiment, the output of the diode detectors 128 is sent to a digital acquisition module 130. As illustrated, the digital acquisition module 130 includes a memory 132 suitable for data storage and a microprocessor 134 which can control the operation of the apparatus 100. Optionally, the memory 132 and/or the microprocessor 134 may also include instructions which allow analysis of the data. In an alternative embodiment, the memory 132 and/or the microprocessor 134 are separate from the digital acquisition module 130. That is, the memory 132 and/or the microprocessor 134 are located in a separate housing from the digital acquisition module 130. In an example embodiment, the digital acquisition module 130 includes wireless communication circuitry 136 that allows wireless communication, for example, with remote a computer 214 (FIG. 6). In an alternative embodiment, the wireless communications circuitry 136 may be contained in a separate module.

FIG. 6 illustrates a system 200 for optical detection of chemical compounds according to an embodiment. In this embodiment, the apparatus 100 is enclosed inside a container or box 202. The container 202 may include a high speed fan 208 for quick drying the sample holders 118. Optionally, a heating system 210 can also be used along with or instead of the fan 208 for drying the sample holders 118. The combination of airflow (the fan 208) and heating (heating system 210) typically works better than aeration or heating alone. Optionally, to attenuate microbial contamination of the apparatus 100, UV light sources (e.g. UV LEDs) 212 may be placed at one or more of the corners of the container 202. In an embodiment, UV light sources 212 are placed in all 8 corners of the container 202. The UV light sources 212 typically are illuminated for sufficient time to kill any microbial contamination. For example, the UV light sources 212 may illuminate the apparatus 100 for one hour after the experiments are over.

As discussed above, apparatus 100 includes wireless communication circuitry 136. With the includes wireless communication circuitry 136, the apparatus 100 can receive instructions and send data to a remote computer 214. The remote computer 214 of system 200, may include workstations, laptops and smaller computing devices such as personal digital assistants (PDA) or even modern cell phones. Indeed, the remote computer 214 includes any device capable of wirelessly sending instructions and receiving data. With the wireless communication circuitry 136, the system 200 can be remotely controlled. That is, the apparatus 100 may be operated by a user who is not in direct physical contact with the apparatus 100.

Referring again to FIG. 6, in an embodiment, solar cells 204 could be used for powering the apparatus 100. Indeed, in some embodiments all of the mechanical and electrical components of the apparatus 100 may be powered by solar cells 204. In alternative embodiments, the apparatus 100 may include batteries 206 and be battery powered. In still other embodiments, the apparatus 100 may include solar cells 204 and rechargeable batteries 206 charged by solar cells 204. Such an embodiment could receive power by solar cells 204 yet still be able to operate under conditions with minimal light.

In alternative embodiment, detection and measurement may be performed by non-optical techniques. That is, the light sources 126 and the light detectors 128 may be replaced with electrical and other techniques. For example, organic molecules may be detected via mass spectroscopy (MS) or nuclear magnetic resonance (NMR). Ions may be detected via atomic absorption.

In the above embodiments, in contrast to conventional devices, turbidity, biologicals, organics, and/or ionic contaminants may be determined with a single device. Further, the apparatus 100 may be operated such that some or all of the stages 108, 110, 112, 114 may be operated substantially at the same time. In this manner, turbidity, biologicals, organics, and/or ionic contaminants may be determined quickly and efficiently.

Example embodiments of the method of using the apparatus 100 will now be described (FIG. 7). In a first step 300 of an embodiment of the method, water is pumped into the apparatus 100 by the pump 106. In one aspect, the pump 106 is a syringe type pump. When the piston of the syringe is withdrawn, suction is created which causes the withdrawal of the water from the pond/lake. In an alternative aspect, the pump 106 may be a peristaltic pump. Other pumps may also be used. As discussed above, the sample holder 118 may include a detachable bottom part, the lower shutter 124. During piston pulls, the lower shutter 124 is closed. When measurement is complete, the lower shutter 124 can be opened, facilitating removal of waste solutions from the sample holder 118.

In an embodiment, the first sample holder 118 used for the measurement of turbidity. That is, the first stage is a turbidity stage 108. In turbidity stage, the measuring unit can contain a high intensity light emitting diode having emission at approximately 660 nm. Other wavelengths may be used, however, 660 nm is distant from the absorption regions of the most common contaminants and therefore 660 nm is suitable for the measurement of the nonspecific scattering by large particles.

The turbidity may be characterized by the rate of sedimentation. The rate of the sedimentation is generally dependent on the mass and volume of the particles. Thus, the slope of the increase in light intensity provides a measure of the rate of sedimentation. From the rate of sedimentation, the size of the dissolved particle can be calculated. The calculation can be done as follows. For free settling, the total amount of force exerted on a particle can be broken down into four forces: Force due to Acceleration=Gravity Force−Buoyancy Force−Drag Force. The buoyancy (as a function of gravity) and drag forces (as a function of acceleration) can be calculated with equations 1 and 2 below.

$$F_G = (\rho_P - \rho) g V_P \qquad 1$$

where $\rho_P$ is density of particle, $\rho$ is density of fluid, $g$ is gravitational constant, $V_P$ is volume of particle.

$$F_D = \frac{C_D A_P \rho v_s^2}{2} \qquad 2$$

where $C_D$ is drag coefficient, $A_P$ is area of particle, $\rho$ is fluid, $v_s$ is settling velocity.

These equations can be combined and solved for the settling velocity $V_s$ as a function of the hydrodynamic size ($V_p/A_p$) of the particles.

$$v_s = \sqrt{\frac{2(\rho_P - \rho) g V_P}{C_D A_P \rho}} \qquad 3$$

Thus, by measuring the settling velocity, the hydrodynamic size of the particles can be calculated.

Additionally, the opacity of the sample may be used to provide a measure of the concentration of the particles. Opacity is generally caused by the absorbance and scattering of larger particles. In an embodiment, absorbance is measured at 660 nm. At this wavelength, there is essentially no loss of light due to absorbance of the particles. That is, the absorbance of the sample is due essentially from scattering from the particles.

The beam of monochromatic radiation directed at a sample solution has an incident radiant power $P_0$. When absorption takes place, the beam of radiation leaving the sample has a radiant power of P. The absorbance of a material can thus be defined in terms of the radiant power of the light transmitted through a sample divided by the radiant power of the light incident on the sample. This relationship is defined in equation 4 below:

$$A = \log_{10} P_0/P \qquad 4$$

Where A is the absorbance, $P_0$ is the radiant power of the incident light and P is the radiant power of the transmitted light. For concentration determinations, $P_0$ is determined experimentally by first using a blank with a standard phosphate buffer saline solution and measuring the output voltage at the detector. The output voltages of samples can then be taken and the absorbance calculated with equation 4.

The concentration of the particles in a sample can be determined as follows. The absorbance may be also be defined in terms of concentration of particles in the sample using the Beer-Lambert law:

$$A = ebc \qquad 5$$

Where A is absorbance, e is the molar absorbtivity with units of $L\,mol^{-1}\,cm^{-1}$, b is the path length of the sample—that is, the path length (in centimeters) of the cuvette in which the sample is contained, and c is the concentration of the compound in solution, expressed in $mol\,L^{-1}$ For the same type of particles, if the path length is kept constant, a calibration curve of absorbance as a function of concentration can be determined. The molar absorbivity can then be determined from the slope of the calibration curve. The molar absorbivity is typically constant for a solution gathered from same source. Using molar absorbivity and a curvette of know width, the concentration can be calculated with equation 5.

Referring to FIGS. 2 and 7 in an embodiment, a portion of the water may be filtered 304 with filtration unit 116a and drawn into a sample chamber 118 of the biological measurement stage 110. An analysis of the biologicals 308 may then be performed. In this step, a light source 126 and light detector 128 are provided which are suitable for detecting biological contaminants such as coliforms. In an example embodiment, the filtration unit 116a has a pore size greater than 2 microns. The filtration unit 116 filters out larger particulate matter but has pores of sufficient size to allow the passage of biological contaminants to the biological measurement stage 110.

In the biological measurement stage 110, the biological matter may be treated with a lysing agent 306 before analysis. A small volume of cell lysing mixture may be added to the water sample 306 The lysing mixtures generally contains a detergent (e.g., Triton X or SDS) in a buffer (e.g., sodium phosphate buffer 0.5 M, pH-7.2). Other lysing mixtures may be used. The samples may be thoroughly mixed by a mechanical stirrer 122. After an incubation period, the optical absorbance may be measured 308 with light at a suitable wavelength, e.g. 280 nm with a UV LED emitting at 280 nm and a diode detector. Alternative wavelengths may also be used, such as 260 nm. Indeed, light of any wavelength for which proteins or DNA can be detected may be used. To determine the approximate number of biological contaminants, the net protein content or the net DNA content may be measured. Both the net protein content or the net DNA content are proportional to the number of cells. A wavelength of 280 nm may be used to detect proteins while a wavelength of 260 nm may be used for detecting DNA.

Between the biological measurement stage 110 and the organic molecule stage 112, a second filtration may be performed 310. In one aspect, the second filtration unit 116b may have a pore size <1 micron. This pore size can eliminate larger particles and larger cells but allows the common non-biological organic contaminants to pass. Some of the most toxic organic compounds, commonly known as "dirty dozen," may be monitored by using such a filter. These 12 chemicals are poly-chlorinated biphenyls, dioxins, furans, aldrin, dieldrin, DDT, endrin, chlordane, hexachlorobenzene, mirex, toxaphene, and heptachlor.

These organic compounds have an absorbance at specific wavelengths in the UV, VIS or IR regions. Thus, light emitting diodes having the emission wavelengths in the regions where the compounds have their absorption may be selected. Seven of the compounds and their absorbance are listed in Table 1 below. The information in Table 1 generally known.

TABLE 1

Table 1 describes the name of the organic contaminants of the pond water and their optical detection process

| Name of the Compound | Absorbance wavelength | Source | Detector |
| --- | --- | --- | --- |
| PBC | 245 nm | UV LED | UV diode detector |
| Furans | 284 nm | UV LED | UV diode detector |
| Dioxin | 7.01 micron | IR laser LED | quantum-cascade detectors |
| endrin | 6.25 micron | IR laser LED | quantum-cascade detectors |
| DDT (nile red fluorescence) | 550 nm | VIS LED | Diode detector at 663 nm |
| aldrin | 8.48 micron | IR laser LED | quantum-cascade detectors |
| dieldrin | 10.98 micron | IR laser LED | quantum-cascade detectors |

Mid-IR detectors have a wide-ranging potential applications in sensing, security, and especially in NIR spectrometry. Indium phosphide (InP)-based quantum-cascade detectors (QCDs) operating from 4 and 17.5 μm are now available. In an embodiment similar to the embodiment illustrated in FIG. 1, the apparatus 100 includes set of seven sample holders 118 for organic analysis, one for each of the seven chemicals list in Table 1. The number of sample holders 118, however, is not restricted. The apparatus 100 may include sample holders 118 for each of the "dirty dozen" organic compounds. Indeed, the apparatus 100 may include sample holders 118 for other compounds as well. Embodiment may also include fewer sample holders 118. Further, one or more of the same holders 118 may be equipped with a reagent reservoir 121. The reagent reservoir 121 may include, for example, a stain. A stain is a compound that bonds to the contaminant and, when excited by a light source, provides light emission in a known wavelength when bound. By adding a stain 312, a contaminant that otherwise is difficult to detect may be detected and its concentration measured 314. For example, for the detection of DDT, a reagent reservoir 121 containing the stain nile red may be provided. The nile red may be added to the water sample in the organic molecule stage 112 to detect DDT 312. Optionally, the mixture may be stirred 313. Other stains useful for the detection of other organic contaminants, of course, may be used as desired.

In some embodiments, the apparatus 100 may include an ion measurement stage 114 and a filtration unit 116c provided between the ion measurement stage 114 and the organic molecule stage 112 for further filtering 316 of the water. The filtration unit 116c may have pores of approximately 0.22 micron. This pore size is suitable for eliminating bigger molecules and compounds but allowing ions through.

The ions may be quantified 320, for example, by a method based on quenching of surface modified Quantum dots specific for the binding of particular ions such as cyanide, copper (II), Fe(II)/Fe(III) etc. In an alternative embodiment, a chemical analysis method may be used for ion detection and measurement. A chemical analysis method, may include additional chemicals and performance of additional reactions. The quantum dots and/or additional chemical reagents may be added 318 via a regent reservoir 121 similarly to the biological measurement 110 and organic molecule stages 112. Optionally, the mixture of quantum dots and water sample may be stirred 319.

Surface modified quantum dots, when excited, fluoresce at a specific wavelength. Further, modified quantum dots may be modified such that they have specificity to bind to a specific ion. In an embodiment, the binding of the ion to the modified quantum dots quenches the fluorescence emission in proportion to the concentration of the ion. Accurate concentration of the ions may be determined with a suitable calibration curve. In one aspect, the fluorescence can be measured by using an LED light source 126 emitting light at the excitation wavelength of the quantum dots and detecting the emission with a diode detector 128 configured for the range of emission wavelength of the quantum dots.

After the completion of the experiments, the pump 106 pumps out the filtration united water. Optionally, the lower shutter 124 may be detached to allow cleaning of the sample holder 118. The sample holders 118 may be washed with the filtration united water pumped with the pump 106.

FIG. 7 illustrates an example embodiment method that comprises the following steps: performing turbidity measurements 302, performing biological measurements 308, performing organic molecule measurements 314, and performing ion measurements 320. In other embodiments, one or more of these measurements is not performed. Further, in other embodiments, one or more of the filtering steps 304, 310, and 316 may be omitted, as can the addition of reagents in steps 306, 312, and 318 and the stirring steps 307, 313, and 319.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "or at least one" and indefinite articles such as "a" or "an" (e.g., "a" and/or "an" should be interpreted to mean "at least one" or "one or more"); the same holds true for the use of definite articles used to introduce claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof.

Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are no intended to be limiting, with the true scope and spirit being indicated by the following claims.

What is claimed:

1. An apparatus comprising:
    a plurality of stages arranged in series and configured to detect contaminants in a sample, wherein the plurality of stages comprises at least a first stage including a first sample holder and a first detector configured to detect a first contaminant and a second stage including a second sample holder and a second detector configured to detect a second contaminant, and wherein the first sample holder comprises a detachable shutter configured to allow selective access to an interior of the first sample holder; and
    a filtration unit positioned between and coupled to an output of the first stage and an input of the second stage;
    wherein one of the plurality of stages is configured to measure turbidity of the sample by monitoring a percentage of light transmitted through the sample as a function of time,
    wherein the one of the plurality of stages comprises an automated stirrer configured to agitate the sample to facilitate a homogeneous solution, and
    wherein the automated stirrer comprises a rotatable bar, and wherein the shutter includes the rotatable bar such that the rotatable bar is connected to the shutter.

2. The apparatus of claim 1, wherein at least one of the plurality of stages is configured to measure a presence of biological organisms in the sample.

3. The apparatus of claim 1, wherein at least one of the plurality of stages is configured to measure a presence of heavy metal ions in the sample.

4. The apparatus of claim 1, wherein at least one of the plurality of stages is configured to measure a presence of an organic compound in the sample, and wherein the organic compound is selected from the group consisting of polychlorinated biphenyls, dioxins, furans, aldrin, dieldrin, DDT, endrin, chlordane, hexachlorobenzene, mirex, toxaphene, and heptachlor.

5. The apparatus of claim 4, wherein the plurality of stages comprises two or more stages configured to detect a plurality of different organic compounds.

6. The apparatus of claim 1, wherein the sample is an aqueous solution.

7. The apparatus of claim 1, wherein the first stage further comprises a light source, wherein the first detector comprises a light detector, wherein the light source comprises a light emitting diode (LED), and wherein the light detector comprises a diode.

8. The apparatus of claim 1, wherein the apparatus is configured to be operated remotely.

9. The apparatus of claim 1, wherein the first stage is configured to measure turbidity of the sample, wherein the second stage is configured to measure a presence of biological organism in the sample, and wherein the plurality of stages further comprises:
    a third stage configured to measure a presence of heavy metal ions in the sample; and
    a fourth stage configured to measure a presence of organic compounds in the sample.

10. The apparatus of claim 1, wherein the plurality of stages further comprise a third stage, and the apparatus further comprises:
    a second filtration unit located between an output of the second stage and an input of the third stage,
    wherein the second filtration unit is configured to filter smaller particles than the first filtration unit.

11. The apparatus of claim 1, wherein the one of the plurality of stages is configured to measure the turbidity of the sample by determining a rate of sedimentation of particles within the sample, and wherein the particles are suspended in an aqueous solution within the sample.

12. The apparatus of claim 1, wherein at least the first or second sample holder comprises a transparent cuvette.

* * * * *

UNITED STATES PATENT AND TRADEMARK OFFICE
CERTIFICATE OF CORRECTION

PATENT NO. : 8,951,783 B2
APPLICATION NO. : 13/254153
DATED : February 10, 2015
INVENTOR(S) : Bhattacharya Page 1 of 2

It is certified that error appears in the above-identified patent and that said Letters Patent is hereby corrected as shown below:

In the Specification

In Column 1, Line 6, delete "stage application" and insert -- stage application filing under 35 U.S.C. §371 --, therefor.

In Column 2, Line 7, delete "systems," and insert -- system, --, therefor.

In Column 2, Line 10, delete "times" and insert -- time --, therefor.

In Column 2, Line 17, delete "where" and insert -- wherein --, therefor.

In Column 2, Line 18, delete "substantial" and insert -- substantially --, therefor.

In Column 2, Line 29, delete "haxachlorobenzene," and insert -- hexachlorobenzene, --, therefor.

In Column 3, Line 19, delete "filtrations" and insert -- filtration --, therefor.

In Column 3, Line 33, delete "cellulose" and insert -- cellulose. --, therefor.

In Column 4, Line 5, delete "shutter 123" and insert -- shutter 124 --, therefor.

In Column 4, Line 22, delete "give" and insert -- given --, therefor.

In Column 4, Line 41, delete "reagent delivery 120" and insert -- reagent delivery system 120 --, therefor.

In Column 4, Line 55, delete "sample" and insert -- samples --, therefor.

In Column 5, Line 56, delete "embodiment," and insert -- embodiments, --, therefor.

Signed and Sealed this
Twenty-first Day of July, 2015

Michelle K. Lee
*Director of the United States Patent and Trademark Office*

In Column 7, Line 36, delete "$L^{-1}$" and insert -- $L^{-1}$. --, therefor.

In Column 7, Line 43, delete "curvette of know" and insert -- curvette of known --, therefor.

In Column 7, Line 59, delete "of cell" and insert -- of a cell --, therefor.

In Column 8, Line 58, delete "Embodiment" and insert -- Embodiments --, therefor.

In Column 8, Line 59, delete "same" and insert -- sample --, therefor.

In Column 10, Line 28, delete ""or at least" and insert -- "at least --, therefor.

In Column 10, Line 32, delete "recitation is" and insert -- recitations. In addition, even if a specific number of an introduced claim recitation is --, therefor.

In Column 11, Line 19, delete "no intended" and insert -- not intended --, therefor.